United States Patent
Lai et al.

(10) Patent No.: US 12,313,523 B2
(45) Date of Patent: May 27, 2025

(54) DEEP LEARNING PARTICLE CLASSIFICATION PLATFORM

(71) Applicants: FlowJo, LLC, Ashland, OR (US); Becton, Dickinson and Company, Franklin Lakes, NJ (US)

(72) Inventors: Janice H. Lai, Mountain View, CA (US); Miguel Velazquez-Palafox, Ashland, OR (US); Ian Taylor, Talent, OR (US)

(73) Assignees: FlowJo, LLC, Franklin Lakes, NJ (US); Becton, Dickinson and Company, Franklin Lakes, NJ (US)

( * ) Notice: Subject to any disclaimer, the term of this patent is extended or adjusted under 35 U.S.C. 154(b) by 1180 days.

(21) Appl. No.: 16/587,909

(22) Filed: Sep. 30, 2019

(65) Prior Publication Data

US 2020/0105376 A1    Apr. 2, 2020

Related U.S. Application Data

(60) Provisional application No. 62/739,796, filed on Oct. 1, 2018.

(51) Int. Cl.
  *G01N 15/14*   (2024.01)
  *G16B 20/40*   (2019.01)
  (Continued)

(52) U.S. Cl.
  CPC ......... *G01N 15/1459* (2013.01); *G16B 20/40* (2019.02); *G16B 40/00* (2019.02); *G16B 50/30* (2019.02)

(58) Field of Classification Search
  None
  See application file for complete search history.

(56) References Cited

U.S. PATENT DOCUMENTS

| | | |
|---|---|---|
| 4,845,653 A | 7/1989 | Conrad |
| 5,739,000 A | 4/1998 | Bierre |

(Continued)

OTHER PUBLICATIONS

Krieg, C., Nowicka, M., Guglietta, S., Schindler, S., Hartmann, F. J., Weber, L. M., Dummer, R., Robinson, M. D., Levesque, M. P., & Becher, B. (2018). High-dimensional single-cell analysis predicts response to anti-PD-1 immunotherapy. Nature medicine, 24(2), 144-153. (Year: 2018).*

(Continued)

*Primary Examiner* — Anna Skibinsky
*Assistant Examiner* — Joseph Pulliam
(74) *Attorney, Agent, or Firm* — Knobbe, Martens, Olson & Bear, LLP

(57) ABSTRACT

Methods and systems for a deep-learning platform for sorting cell populations. An example method includes executing a software-platform associated with analyzing received flow cytometry data obtained via an acquisition device in communication with the computing system, and the software-platform sorting cell populations indicated in the flow cytometry data. User input is received indicating selection of a deep-learning module, the deep-learning module being obtained via a network to supplement the software-platform. The flow cytometry data is analyzed and a machine learning model is selected which was trained based on similar phenotype information as indicated in the flow cytometry data. The machine learning model is applied based on the flow cytometry data, the information being normalized based on the UMI counts associated with the flow cytometry data. A graphical representation of cell populations indicated in the flow cytometry data is presented, the graphical representation sorting the cell populations according to phenotype information.

19 Claims, 8 Drawing Sheets

(51) Int. Cl.
   *G16B 40/00*   (2019.01)
   *G16B 50/30*   (2019.01)

(56) References Cited

U.S. PATENT DOCUMENTS

| | | |
|---|---|---|
| 5,795,727 A | 8/1998 | Bierre |
| 6,014,904 A | 1/2000 | Lock |
| 6,944,338 B2 | 9/2005 | Lock |
| 2012/0245889 A1 | 9/2012 | Zhu |
| 2018/0247195 A1 | 8/2018 | Kumar et al. |

OTHER PUBLICATIONS

McQuin, C. (2018). CellProfiler 3.0: Next-generation image processing for biology. PLoS biology, 16(7), e2005970. (Year: 2018).*

Hennig, H., Rees, P., Blasi, T., Kamentsky, L., Hung, J., Dao, D., Carpenter, A. E., & Filby, A. (2017). An open-source solution for advanced imaging flow cytometry data analysis using machine learning. Methods (San Diego, Calif.), 112, 201-210. (Year: 2017).*

Newman, A. M., Liu, C. L., Green, M. R., Gentles, A. J., Feng, W., Xu, Y., Hoang, C. D., Diehn, M., & Alizadeh, A. A. (2015). Robust enumeration of cell subsets from tissue expression profiles. Nature methods, 12(5), 453-457. (Year: 2015).*

Carpenter, A. E., Jones, T. R., Lamprecht, M. R., Clarke, C., Kang, I. H., Friman, O., Guertin, D. A., Chang, J. H., Lindquist, R. A., Moffat, J., Golland, P., & Sabatini, D. M. (2006). CellProfiler: image analysis software for identifying and quantifying cell phenotypes. Genome biology, 7(10), R100. (Year: 2006).*

Rostam, H. M., Reynolds, P. M., Alexander, M. R., Gadegaard, N., & Ghaemmaghami, A. M. (2017). Image based Machine Learning for identification of macrophage subsets. Scientific reports, 7(1), 3521. (Year: 2017).*

Zeisel, A. Molecular Architecture of the Mouse Nervous System. Cell, 174(4), 999-1014.e22. (Year: 2018).*

Nitta N, Sugimura T, Isozaki A Intelligent Image-Activated Cell Sorting. Cell. Sep. 20, 2018;175(1):266-276.e13 (Year: 2018).*

Arvaniti, E. & Claassen, M. Sensitive detection of rare disease-associated cell subsets via representation learning. Nat. Commun. 8, 14825 (2017). (Year: 2017).*

Luo, Gang. "A review of automatic selection methods for machine learning algorithms and hyper-parameter values." Network Modeling Analysis in Health Informatics and Bioinformatics 5.1 (2016): 1-16. Web. (Year: 2016).*

Yu, Jessica S et al. "CellSort: A Support Vector Machine Tool for Optimizing Fluorescence-Activated Cell Sorting and Reducing Experimental Effort." Bioinformatics (Oxford, England) 33.6 (2017): 909-916. Web. (Year: 2017).*

Bauer et al. (eds.), 1993, Clinical Flow Cytometry: Principles and Applications, Williams & Wilkins, Baltimore, Maryland.

Bornstein et al., Jul. 18, 2018, Single-cell mapping of the thymic stroma identifiers IL-25-producing tuft epithelial cells, Nature, 559(7715):622-626.

Hatcher et al., Apr. 27, 2018, A survey of deep learning: platforms, applications and emerging research trends, IEEE Access, 6:24411-24432.

Jaroszeski et al. (eds.), 1998, Flow Cytometry Protocols, Methods in Molecular Biology No. 91, Humana Press, Totowa, New Jersey.

Landy et al. (eds.), 1993, Clinical Flow Cytometry, Annals of the New York Academy of Sciences, 677(1).

Makhzani et al., Jun. 7, 2015, Winner-Take-All Autoencoders, 11 pp.

Ormerod (ed.), 1994, Flow Cytometry: A Practical Approach, Oxford Univ. Press, Oxford, England.

Shapiro, 2003, Practical Flow Cytometry, 4th ed., Wiley-Liss, Hoboken, New Jersey.

International Search Report and Written Opinion dated Nov. 29, 2019 in application No. PCT/US2019/053880.

* cited by examiner

DEEP LEARNING PARTICLE CLASSIFICATION PLATFORM

CROSS-REFERENCE TO RELATED APPLICATIONS

This application claims priority to U.S. Prov. Patent App. 62/739,796, which was filed on Oct. 1, 2018 and which is entitled "DEEP LEARNING PARTICLE CLASSIFICATION PLATFORM". U.S. Prov. Patent App. 62/739,796 is hereby incorporated by reference herein in its entirety.

Any and all applications for which a foreign or domestic priority claim is identified in the Application Data Sheet as filed with the present application are hereby incorporated by reference in their entirety under 37 CFR 1.57.

INCORPORATION BY REFERENCE

This application hereby incorporates herein by reference the following patents in their entities: U.S. Pat. Nos. 4,845,653, 5,739,000, 5,795,727, 6,014,904, and 6,944,338. This application additionally incorporates herein by reference U.S. Patent Pub. No. 2012/0245889 in its entirety.

BACKGROUND

An example technique for analyzing flow cytometry data includes gating via a software-based tool. For this example technique, a user may interact with a user interface presenting graphical depictions of populations of cells with common characteristics. Example characteristics may include marker expressions, forward scatter, and so on. Example graphical depictions may include plots associated with the flow cytometric data, such as a contour plot, density plot, and so on. The user may thus analyze the graphical depiction and perform a gating process. As an example, the user may leverage certain gating tools which may be accessible via the user interface. These gating tools may help to subdivide the populations of cells. For example, the user interface may indicate areas of maximum events. In this example, the maximum events may indicate a maximum number of events for a population of cells.

However, conventional user interfaces and software-based techniques for performing gating introduce technical issues. For example, a user may be required to spend a substantial amount of time interacting with the user interface. Indeed, the gating tools may introduce technical complexities which require a user to learn each gating tool's specific functionality. Furthermore, these software-based techniques may introduce variability depending on the specific user utilizing the software-based tool. As an example, a first user may subdivide populations of cells in a different manner as compared to a second user.

SUMMARY

Described herein are techniques to perform substantially automated analyses of populations of cells. As will be described, supervised learning techniques may be leveraged to improve upon prior software-based tools used for particle classification. Example supervised learning techniques may include deep learning based techniques, support vector machines, and so on. Through the use of the techniques described herein, a usability of such software-based tools may be enhanced. For example, a tool described herein may substantially reduce a variance associated with different users performing gating of populations of cells. Thus, and in contrast to prior software-based tools, these users may receive a same, or substantially similar, analysis of input populations of cells.

It may be appreciated that performing analyses of particles, such as populations of cells, may be of great technical importance. For example, research work may depend on such analyses. As another example, health information for people may depend greatly on an accuracy, and repeatability, of such analyses. Current techniques to perform such analyses suffer from several technical deficiencies. For example, and as described above, different users of prior software-based tools may arrive at different analyses of a same set of input data. Additionally, these prior software-based tools may take substantial time to perform analyses.

In contrast, an example software-based tool described herein (also referred to as a platform) may provide a standardized workflow which may be reliably leveraged by users. As will be described, a user of the software-based tool may provide input data according to disparate formats. Advantageously, a particular machine learning model may be selected by the software-based tool for use in analyzing the input data. As an example, a first machine learning model may be advantageous for a certain population of cells while a second machine learning model may be advantageous for a different population of cells. In this way, the software-based tool may automatically select a machine learning model which may enable a most accurate analysis. Additionally, the software-based tool may adjust the input data according to a standardized scheme. For example, the software-based tool may normalize the data, or otherwise clean the data, according to particular techniques. An example such a technique may include Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above-and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

DETAILED DESCRIPTION

Introduction

Figure 1A:
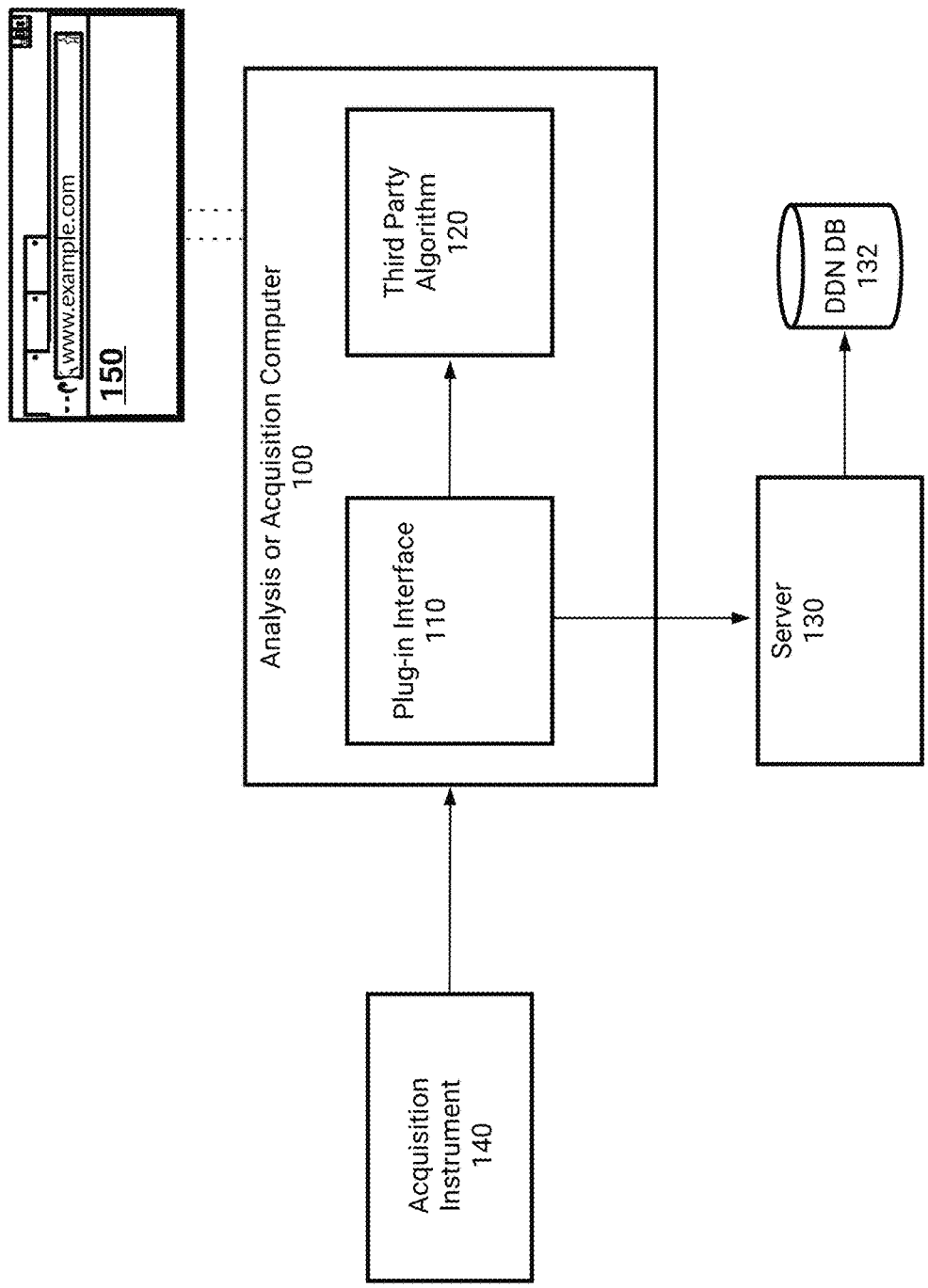
FIG. 1A illustrates an example system architecture which may implement the techniques of some embodiments described herein.

Particle analyzers, such as flow and scanning cytometers, are analytical tools that enable the characterization of particles on the basis of electro-optical measurements such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection. A multiplicity of different particles or components may be simultaneously detected by using spectrally distinct fluorescent dyes to label the different particles or components. In some implementations, a multiplicity of photodetectors, one for each of the scatter parameters to be measured, and one or more for each of the distinct dyes to be detected are included in the analyzer. For example, some embodiments include spectral configurations where more than one sensor or detector is used per dye. The data obtained comprise the signals measured for each of the light scatter detectors and the fluorescence emissions.

Particle analyzers may further comprise means for recording the measured data and analyzing the data. For example, data storage and analysis may be carried out using a computer connected to the detection electronics. For example, the data can be stored in tabular form, where each row corresponds to data for one particle, and the columns correspond to each of the measured features. The use of standard file formats, such as an "FCS" file format, for storing data from a particle analyzer facilitates analyzing data using separate programs and/or machines. Using current analysis methods, the data typically are displayed in 1-dimensional histograms or 2-dimensional (2D) plots for ease of visualization, but other methods may be used to visualize multidimensional data.

The parameters measured using, for example, a flow cytometer typically include light at the excitation wavelength scattered by the particle in a narrow angle along a mostly forward direction, referred to as forward scatter (FSC), the excitation light that is scattered by the particle in an orthogonal direction to the excitation laser, referred to as side scatter (SSC), and the light emitted from fluorescent molecules in one or more detectors that measure signal over a range of spectral wavelengths, or by the fluorescent dye that is primarily detected in that specific detector or array of detectors. Different cell types can be identified by their light scatter characteristics and fluorescence emissions resulting from labeling various cell proteins or other constituents with fluorescent dye-labeled antibodies or other fluorescent probes.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1994); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

The data obtained from an analysis of cells (or other particles) by certain particle analyzers, such as a multi-color flow cytometry, are multidimensional, wherein each cell corresponds to a point in a multidimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots," of the data. Alternatively, clusters can be identified, and gates that define the limits of the populations, can be determined automatically. Examples of methods for automated gating have been described in, for example, U.S. Pat. Nos. 4,845,653; 5,739,000; 5,795,727; 6,014,904; and 6,944,338; and U.S. Pat. Pub. No. 2012/0245889, each incorporated herein by reference in their entireties.

In this specification, flow cytometry data is thus to be interpreted broadly. For example, flow cytometry data may comprise information obtained via an acquisition device (e.g., particle analyzers, flow cytometer, and so on). In general, events may be received from an acquisition device which indicate information associated with cells. For example, events may indicate information associated with single cells. As an example, phenotype information (such as a presence or level of a cell surface marker, and/or a gene expression level such as an mRNA expression level or protein expression level), reagent information, and so on, may be included in the events.

Enhanced Learning Techniques

Deep learning is a subset of machine learning. One difference pertaining to neural networks as compared to other machine learning is a depth and complexity of the architecture. This depth and complexity, when properly trained, is how the neural network "learns" complex interactions. As may be appreciated, a neural network may comprise a multitude of layers. Example layers may include convolutional layers, in which volumes of convolutional filters may be applied, and fully-connected (e.g., dense) layers. Each layer may be defined, at least in part, by certain parameters. Example parameters may include biases, weights, and so on. Additionally, a neural network may be defined, at least in part, by certain hyperparameters.

Example hyperparameters may include a number of layers, a number of neurons per layer, activation functions, a dropout rate, and so on.

A software-based platform described herein may advantageously leverage one or more neural networks to perform an enhanced gating process. Additionally, and as will be described, the software-based platform may enable the rapid training of new neural networks However, even with these advances, researchers cannot reproducibly classify cell phenotypes from FCM and scRNA-Seq data using traditional machine learning methods outlined. Secondly, traditional methods are domain-specific, our approach works on truly multi-omics datasets, including clinical EHR and literature NLP. Furthermore, the tools outlined can be computationally expensive thus making them less useful for mainstream science due to the resource needed to train and apply the machine learning.

To address these and other issues with particle classification, feature a DL-based particle type classification platform for FCM, scRNA-seq, and other multi-omic datasets are provided. The platform provides a flexible modeling system to publish and identify a deep learning model for a particular experiment. The platform may include transforms and normalization features to correct inherently noisy data. The platform may include features to correct batch effects and type II (e.g., false negative) errors. The platform may include features for training user defined-models or auto-machine learning to create a model a specific experiment or researcher using artificial intelligence. The platform may provide models that classify cells or other particles based on information beyond the event data such as using an expert's knowledgebase. The model may distinguish features using stacked autoencoders (SAE). One example autoencoder is a winner take all (WTA) autoencoder that may be trained to classify events for a targeted panel. Further discussion of winner take all autoencoders may be found in "Winner-Take-All Autoencoders" by Makhzani and Frey (2014). The plug-in may cause clustering, dimensionality reduction, and feature selection using one model identified either by the researcher or based on properties of the experiment. The plug-in may generate or present via a user interface model performance, classification of events, and regression results for the data set.

Overview of Example System/Example User Interface

Referring to the accompanying drawings in which like reference numbers indicate like elements, FIG. 1A illustrates a system diagram. As shown in FIG. 1A, a data acquisition instrument 140 is connected to an analysis or acquisition computer 100. In an example embodiment, the acquisition instrument 140 is a particle analyzer such as a flow cytometer. However, it should be understood that instruments other than flow cytometers may be used as the acquisition instrument 140. For example, instruments for single cell gene and/or protein expression analysis, such as a BD RHAPSODY™ Single-Cell Analysis system may also be used. However, for the purpose of explanation, flow cytometry will be used as an example embodiment to illustrate the innovative and useful features with regard to single cell technologies including flow cytometry.

While FIG. 1A illustrates an acquisition computer 100, it is to be appreciated that the computer 100 may be a user device of one or more processors. For example, the user device may be a laptop, tablet, mobile device, wearable device, and so on. In this example, the user device may perform analyses via a software-based tool or framework executing on the user device. Optionally, the user device may access a web page associated with a web application. The web page may provide a front-end interface into the techniques described herein. Optionally, the user device may execute an application associated with performing analyses. In this example, the application may receive information from the acquisition instrument 140. The application may then perform analyses, such as via a forward pass of one or more machine learning models using the received information.

In some embodiments, the above-described user device may receive information from the acquisition instrument 140 and provide it to an outside system for processing. For example, the user device may provide (e.g., upload) received information to the outside system via a network (e.g., the internet). The user device may then receive analyses from the outside system as described herein. In this way, the processing may be offloaded onto the outside system (e.g., a cloud-based computing system).

In some embodiments, the acquisition computer 100 may receive information, such as a dataset, from a user of the computer 100. For example, the received information may comprise event data. As an example, disparate datasets may be generated using particle analyses, flow cytometers, and so on. These datasets may thus include tabular data (e.g., comma separated values) according to one or more schemas. For example, the datasets may be stored according to a particular format (e.g., SeqGeq). As another example, the datasets may be stored as including identifiers of cells along with different measures associated with markers.

The analysis computer 100 is connected to a server 130 through a network connection, such as over the internet, over a subnet, over an intranet, or through the internet to a cloud-based network. In some embodiments, the acquisition instrument 140 may be connected to an acquisition computer 100, and the data acquired by the acquisition instrument 140 is analyzed on the analysis computer 100 after transferring the data to the analysis computer 100.

The analysis computer 100 executes analysis software, and the analysis software may be capable of adjusting one or more parameters (e.g. voltage, flow rate, etc.) of the acquisition instrument 140 for a sample being tested. Such analysis software may also display initial sample information while acquiring sample data to provide feedback for a user to assess whether the parameters are correctly set. The analysis software may vary depending on the manufacturer of the acquisition instrument 140. In some embodiments, the acquisition computer 100 may execute a light version of the analysis software containing mostly user-interface items, and the server 130 also includes a version of the analysis software. In this embodiment, the server 130 may perform the processing-intensive functions, such as heavy data analysis because the server 130 may have more computing resources than the acquisition computer 100.

The analysis software may receive data signals from the acquisition instrument 140 indicating results of a sample being analyzed by the acquisition instrument 140, or the analysis software may receive a data file representing the data collected by the acquisition instrument 140. In some embodiments (for example, when the acquisition instrument 140 is a flow cytometer), the data generated by the analysis software may indicate any or all of the number of cells in a sample, the number and frequency of certain cell types, such as the number or frequency of peripheral blood mononuclear cells (PBMC), the number or frequency of CD4+ T cells, the number of CD14 cells, the number or frequency of CD7+ cells, etc. The results of a sample analysis may be contained within one or more flow cytometry standard format files (e.g., a FCS or CSV file). The acquisition computer 100 creates an FCS file based on the signals and data provided by the acquisition instrument 140. However, it should be understood that other file formats may be used, particularly if the acquisition instrument 140 is not a flow cytometer. The analysis software may further generate metadata about the sample that indicates things such as acquisition instrument ID, patient ID, acquisition conditions and parameters, etc.

The analysis computer 100 also includes an interface 110 that permits the analysis computer to communicate with remote computers, such as an analysis server or a third party server. As an example of the other computer to which the acquired data is transferred, the server 130 may be a remote server dedicated to flow cytometry analysis. In the remote server embodiment, the analysis or acquisition computer 100 may access the server 130 over a network. The analysis or acquisition computer 100 may also communicate with third party computer systems or servers. The analysis or acquisition computer 100 may store and execute third party algorithms 120, such as algorithms configured to identify populations, to include tracking identification numbers for clinical purposes, or any other external algorithm capable of analyzing data or processing data generated by the acquisition computer 100. As described herein, example algorithms 120 may include machine learning models. For example, convolutional or fully-connected neural networks may be used to analyze data.

While FIG. 1A illustrates an example in which the analysis or acquisition computer 100 system stores and executes a third party algorithm 120, it should be understood that a remote computer, such as the server 130, may also execute the third party, or "external", algorithms. The acquisition computer 100 may communicate with multiple remote computer systems depending on the needs and analysis performed by the acquisition computer 100.

The server 130 comprises a processor and memory as well as data storage, such as a database. Processor-executable instructions resident on a non-transitory computer-readable storage medium (such as memory) may be executed by the processor to perform tasks described herein. The database may store data discovery node data structures, which are described herein. The acquisition computer 100 may similarly comprise a processor and a memory, and wherein processor-executable instructions resident on a non-transitory computer-readable storage medium (such as memory of the acquisition computer 100) may be executed by the processor of the acquisition computer 100 to perform tasks described herein for the acquisition computer 100.

The description that follows will elaborate on a number of different aspects of (1) a plug-in framework and interface 110 for invoking and assimilating external software algorithms, and (2) a deep learning plug-in that predicts particle type based on pre-trained models from neural net machine learning. For example, the plug-in may receive, as an input, a single-cell dataset (AbSeq, scSeq, or Ab) of interest, may choose a model from available models, and may automatically generate one or more of: fully annotated populations of events for the dataset, validation metrics, and identified gene sets of interest.

Optionally, the plug-in may select a particular machine learning model based on analyzing input information. For example, certain machine learning models may have been trained based on certain cell populations and/or phenotype information. The input information may identify particular phenotype information, markers, reagents, and so on. Example phenotype information may include surface markers, receptors, antigens, and/or expression levels such as an mRNA expression level or protein expression level, and so on. Thus, the machine learning models may be trained to sort populations of particles such as cellsbased on event data, for example phenotype information. For example, a particle analyzer may be directed to physically sort different cells into different locations based on phenotype information classified by the plugin. In this way, the plug-in may select a particular machine learning model which is optimized, or otherwise advantageous, for the input information. For example, if the input information indicates that certain reagents were used, the plug-in or system may determine that a machine learning model suited (e.g., trained) to assign certain classifications is preferable.

Within the study of single cell assays, scientists and algorithmists continue to generate useful analysis algorithms that streamline analysis of data collected by an acquisition instrument 140. For example, some external analysis algorithms are configured to identify cell populations.

Conventionally, cell population identification is done manually through a process called gating. Manual gating generally involves a user manually drawing a shape, such as a circle or polygon, around a set (cluster) of data points to identify a cell population. However, advances in life science data analysis have generated automatic gating programs capable of identifying cell populations. Furthermore, the use of a computer processor for cell population identification or any other data analysis step may remove any human-created bottlenecks or biases because the processor-executed algorithms can identify cell populations or conduct other analysis faster and more objectively than manual analysis performed by a human. While population identification algorithms have been given as an example, other types of data analysis algorithms exist that help scientists analyze and interpret data collected by acquisition instruments, such as external algorithms for generating reports or visualizing analysis results and high-throughput genomic and phenomic data analysis such as SPADE, FlowMeans, and algorithms hosted as part of the Bioconductor project.

In addition to external algorithms 120 for population identification, the algorithm plug-in framework and interface 110 may communicate with an external server 130 or remote computer systems to download experiment data from open-source databases, download annotated experiment data from external databases, upload workspace data so that the external server 130 or remote computer system may scan for statistic values, execute application level operations, or to receive tracking identification numbers for clinical trials. The ability to interact with external server 130 systems provides the analysis software with valuable pre- and post-processing of analysis results. For example, if a scientist conducting a clinical trial needs a trial identification number, the algorithm plug-in framework and interface 110 may communicate with the external server 130 to upload clinical trial experimental results for verification purposes.

In yet another embodiment, algorithms 120 that are internal to the analysis software may be compartmentalized in a specific platform, making them inaccessible outside their intended context. Examples of these internal, but inaccessible outside their intended context, algorithms (when the analysis software is, for example, FlowJo) may include polynomial fits in a Proliferation platform, +/−peak finding in FlowJo's Compensation Editor, or Gaussian fitting in FlowJo's cell cycle platform. The algorithm plug-in framework and interface 110 described herein not only integrates the external algorithms to the analysis software but also allows for the use of compartmentalized internal algorithms outside of their current, limited context described above.

A plugin system is a mechanism that provides an API to enable external algorithms to run in a product to extend its functionality. External algorithms can typically be used to identify populations by generating a resultant CLR/CSV file (where each row corresponds to an event in the sample), but may also generate additional artifacts, such as reports or tables. In example embodiments, the external algorithm can be implemented in the Java language, or in any other language that can be invoked from Java. To add an external algorithm, the developer will implement a Java interface that is used by the FlowJo product to create a new 'population node' in the workspace, that can then be manipulated like FlowJo's geometrically-gated population nodes to create graphs and statistics.

As shown in FIG. 1A, the acquisition computer 100 may store and execute a plurality of software programs and algorithms 120 useful in analysis of data acquired by the acquisition instrument 140. For example, the analysis software may include a single cell analysis program, such as FlowJo. The third party algorithms 120 may perform processing complementary to the analysis software, such as, but not limited to, automatic population identification programs, deep learning particle classification, or external server 130 functions described above. The acquisition computer 100 may execute the external algorithm 120 at the direction of the analysis software. In some embodiments the acquisition computer 100 may execute the external algorithms 120, and in another embodiment, a remote computer, such as the server 130 shown in FIG. 1A, may execute an external algorithm and provide the results of the external algorithm's processing to the acquisition computer 100 over a network.

In this way, the acquisition computer 100 (e.g., a user device of one or more processors) may execute a software-based tool or platform associated with analyzing cell populations. As an example, the software-based tool or platform may be the FlowJo platform. Thus, this software-based tool or platform may provide complex functionality associated with importing, analyzing, and presenting, cell population information. This software-based tool or platform may enable the inclusion of different plug-ins or modules as described above. For example, a user of the software-based tool or platform may access an online store associated with obtaining plug-ins or modules. In this example, the online store may be accessible via the software-based tool or platform. The online store may additionally be accessible via a web page or application. A user may then select from among the particular plug-ins or modules.

Advantageously, one or more of the plug-ins or modules may be enable the deep-learning techniques described herein. For example, particular deep-learning models may be obtained by a user. The models may optionally be obtained as code to be interpreted (e.g., TensorFlow code, optionally with a Keras frontend), as executable files, as definitions of models (e.g., parameters, hyperparameters), and so on. In some embodiments, a particular plug-in or module may be obtained which is a frontend into the deep-learning based analyses described herein. For example, the particular plug-in or module may update a frontend interface associated with the software-based tool or platform.

As an example, a toolbar of the software-based tool or platform may be updated to reflect that deep-learning based analyses may be performed. A user of the software-based tool or platform may thus select this plug-in or module. In response, the plug-in or module may allow for analyses by different machine learning models to be performed on input information. User interface 150 may, in some embodiments, represent a user interface with which a user may interact.

Figure 1B:
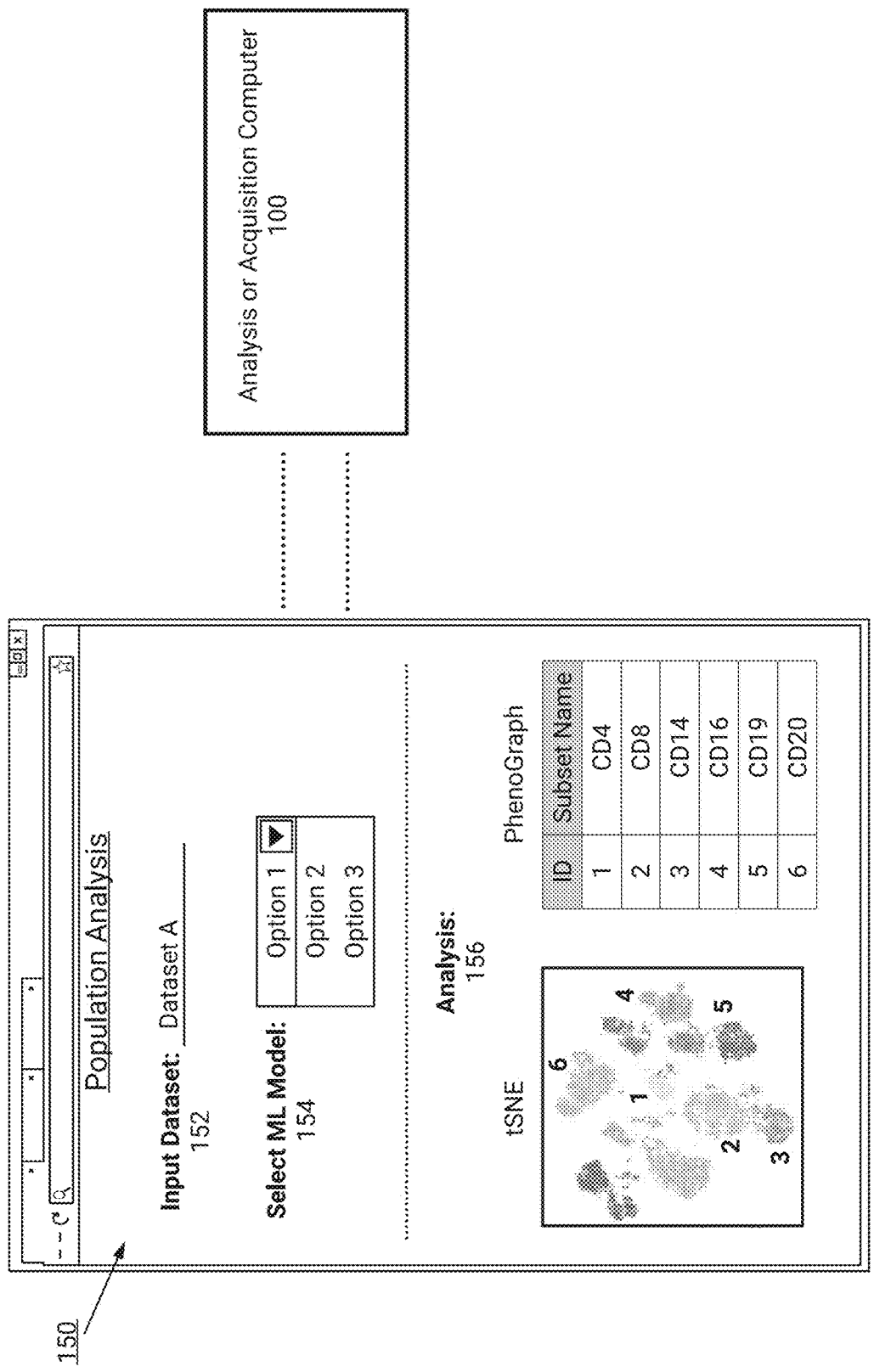
FIG. 1B illustrates an example user interface associated with analyzing cell or particle information of some embodiments described herein.

FIG. 1B illustrates an example user interface 150 associated with analyzing cell or particle information. In this example, immune cell information is sorted (e.g., CD4, CD8, CD14, CD16, CD19, CD20, and so on). The user interface may be an example of a user interface generated by a software-based tool or platform. For example, the user interface may be generated by software, or an application, executing on a user device, such as the acquisition computer 100. The user interface 150 may also be generated by a web browser executing on the user device. For example, the user interface 150 may be associated with a web application executing on an outside system.

In the illustrated example, the user interface 150 includes functionality to perform a "Population Analysis." A user of the user interface 150 may specify a particular dataset which is to be analyzed via interactive portion 152. For example, the user may provide user input to the interactive portion 152 to cause selection of a dataset. In this example, the user input may include keyboard/mouse input, touch-based input, verbal commands, and so on. Optionally, the user interface 150 may cause access to a storage system, or an acquisition instrument, to receive information to be analyzed. With respect to a storage system, the user interface 150 may present available files or information which may be selected.

The user interface 150 further includes a model portion 154 with which a user may select a particular machine learning model. As described herein, particular machine learning models may be advantageous depending on the information to be analyzed. Thus, a user device or system (e.g., system 100) may automatically select a particular machine learning model. In some embodiments, available machine learning models may be associated with certain metadata, textual descriptions, and so on. Thus, the user interface 150 may present a particular model which is appropriate for the input information. As described above, the input information may include information indicating surface markers, cell identifiers, and so on. Thus, this input information may be used to select the particular model. Optionally, a user of the user interface 150 may select from among a multitude of options as illustrated.

Optionally, a machine learning model may be specific to certain classification of cells (e.g., immune cells). Optionally, a machine learning model may be used to with a multitude of classifications or types of cells. For example, the machine leaning model may be a general model to sort populations of cells based on phenotype.

As will be described, the input information may additionally be normalized. An example step during normalization may include pooling the input information and then performing a transformation of unique molecular identifiers (UMI) counts. Thus, this normalization scheme may allow for a particular machine learning model to be selected based on the UMI counts.

User interface 150 further includes an analysis portion 156. The analysis portion may be generated, at least in part, based on a particular machine learning model. For example, the machine learning model may perform a forward pass of the input information. It may be appreciated that the machine learning model may include a final layer associated with classifying the input information. As a non-limiting example, a softmax layer may be used. Thus, the machine learning model may assign particular classifications to input information. In the illustrated example, a machine learning model has assigned classifications to different populations of cells (e.g., classifications 1-6). These populations of cells may be graphically depicted 158A. A representation 158B of the classifications, or label information, is additionally included. This representation 158B may associate an identifier of a classification illustrated on the graphical depiction 158A with a corresponding population of cells.

The user interface 150 may include information identifying unbiased clusters of cells, for example based on the applied machine learning model's classification assignment or prediction per cell. This information may be annotated with corresponding cell classifications. Additionally, the user interface 150 may include a summary metric of median, or other measure of central tendency, cell classifications. For example, scores may be presented for each classification. In some embodiments, a heat-mapped confusion matrix may be generated and/or presented. In some embodiments, gene sets associated with each cell classification predicted may be presented and/or generated.

Advantageously, the machine learning models accessed via the user interface 150 are trained. Thus, they may analyze the input information and generate output information (e.g., labels corresponding to classifications 1-6). In some embodiments, users of the software-based platform or tool may generate their own models. For example, the users may run a search through different hyperparameters to identify a machine learning model which is accurate for certain input information. In this example, the input information may be separated into a training and validation set. Machine learning models may be trained according to the training set, and then accuracy determined based on the validation set.

In some embodiments, a user may upload a certain accurate machine learning model for use by other users. For example, the other users may download the machine learning model via an online store, module, plug-in, and so on. As another example, the user interface 150 may automatically select a machine learning model which has been uploaded by another user. In some embodiments, a back-end server system (e.g., server 130) may validate an uploaded machine learning model. In some embodiments, the back-end server system may aggregate training information across a multitude of users. As an example, a user who trains a new machine learning model may indicate phenotype information, cell type information, and so on.

In this way, the back-end server system may aggregate information to train an updated model with enhanced training information. In all situations in which aggregation of training data occurs, it may be appreciated that users may indicate affirmative consent and/or otherwise opt-in.

Figure 2:
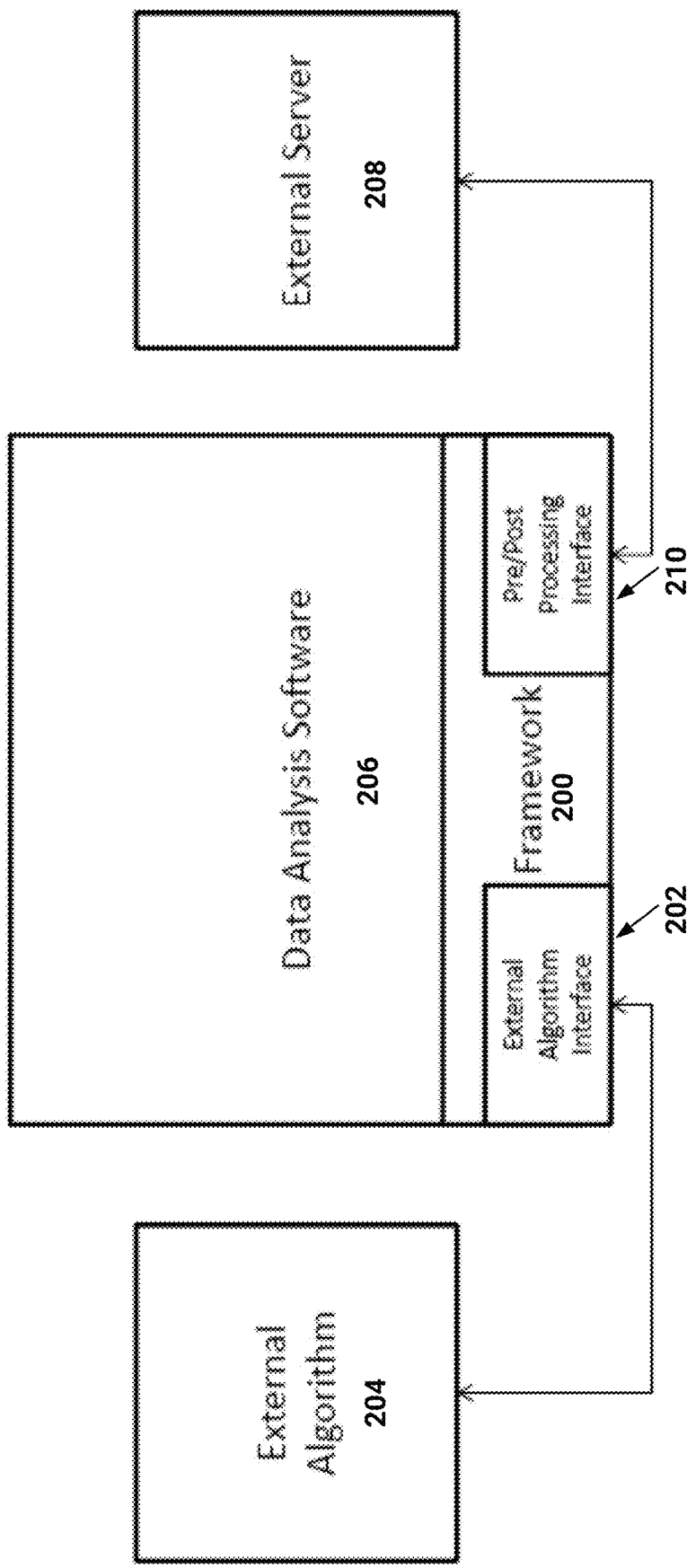
FIG. 2 illustrates an exemplary framework and interface for invoking a processing of analysis results within a session of an example software-based analysis tool of some embodiments described herein.

FIG. 2 illustrates an exemplary framework 200 and interface for invoking an external algorithm or pre/post-processing of analysis results within a session of the analysis software's processing. The framework 200 described herein may build upon existing scientific data analysis software. For example, if the analysis software is software generated for analyzing flow cytometry data, the framework may call upon an external algorithm to identify cell populations within data gathered by a flow cytometer. The framework for interacting with external servers and external algorithms may be included within the data analysis software.

For example, the framework 200 may include a collaborating set of classes and their sequence of interactions, as defined by a programming language such as Java. While Java is given as an example programming language, one of any number of programming languages may serve as the programming language that executes the processes and framework described herein. While multiple programming languages may achieve the system and method described herein, Java does have certain advantages that make it desirable over other programming languages, namely Java's ability to call out to other programming languages, such as C, R or a web-based calculation engine language. Many external algorithms that perform statistical analysis of data collected by scientific instruments are written in the R language. Thus, Java's ability to call out to R bridges the analysis software to an external algorithm written in R. Of course, if the external algorithm is not written in R, Java may also call out to the external algorithm's programming language.

The framework provides the mechanism by which current and future data analysis algorithms are invoked with an input set of data values, as well as the subsequent processing of analysis results, in the form of event cluster values, formulas, visual graphics, or geometrically-defined boundary definitions. In other words, the framework 200 generates a set of input data and calls upon an interface to communicate the input data to an external algorithm or an external server. After the external algorithm's processing, the framework may receive analysis results from the external algorithm or server and provide a mechanism by which the invocation of the algorithm or pre/post processing is represented and saved in a file. The analysis results saved in the file can be integrated with the analysis software for downstream statistical calculations, graphing or generation of other visualizations of the results, or invocation of other algorithms (such as additional external algorithms, subsequent pre/post-processing, or algorithms included within the analysis software).

The framework 200 can manages invocation of integrated algorithms, which are algorithms that are external to the data analysis software itself. The analysis software provides an interface 202 through which researchers can interact with these algorithms 204. The analysis software 206, based on the instructions provided by both the researcher (e.g. selecting a particular population on which an analysis is to be run) and the plugin developer (e.g., specifying the requirements for the data which the algorithm needs as input (e.g. a CSV file corresponding to the data values of the population which the biologist has selected) and, following an analysis, where and what type of output will be available for the plugin interface to present to the user). The interface also serves as the agent through which updates in analysis are communicated, such that analysis always stays hierarchically correct and biologically relevant. More specifically, not only does the framework invoke integrated algorithms when an analysis is first run, but the framework may re-execute an integrated algorithm whenever the input set of data values change or, in the case of deep learning, when the underlying neural network model changes. Therefore, operators can run analysis quickly on multiple sets of data inputs, and the framework will invoke and re-execute the integrated algorithms without user interaction anytime the input data values change, the user changes experiment parameters, or the underlying model is updated. For example, changing some data parameters may change how populations are identified by an integrated algorithm. Upon noticing a change in data input, the framework invokes the integrated algorithm to re-identify the populations, and the framework uses the analysis results generated by the integrated algorithm. Upon receiving the analysis results from the integrated algorithm, the framework may provide the results to the analysis software in a data format understood by the analysis software, and the analysis software may perform downstream analysis on the results, such as statistical analysis, graphing, or reporting.

The framework 200 allows algorithm integration to be saved as a workspace so that workspaces may be saved and re-opened for further analysis.

The framework may include an interface for communicating with remote computer systems and an interface for communicating with external algorithms. Each interface provides a means by which external algorithms or functions stored on external servers 208 may be invoked without user interaction. In fact, to the user viewing the data processing through a graphical user interface, the invocation of an external algorithm 204 may be invisible, as only the results of the analysis performed by the external algorithm 204 may be shown to the user, such as through statistics, graphs, or other reports generated by the analysis software 206.

Generally, the interfaces for invocation of the integrated algorithms include, but are not limited to, an input file of data values, an output folder destination, and an XML description of a data set from one or multiple experiments. This XML description may include pointers to raw data, all analysis executed including plugin-driven analyses, meta-information about the data, and data transformations that are optimally used to process and visualize the data such as logicle, biexponential, hyperlog, and hyperbolic arcsin. In the case of generating a new neural network, the description may include boundaries for generating or training the neural network model such as hyper-parameters, the number of network layers, and target model accuracy. The XML description may take the form of an XML document that specifies this information via markups hierarchically links raw data to the analysis and associated results. It should be understood that forms other than XML may be used, such as proprietary binary files which can store the same data and analysis architecture.

Furthermore, the description of the data set, whether in XML or another format, can include the metadata regarding input parameters for any plugin-based analyses and pointers to any derivative data produced by the external algorithms. Whether the XML meta-information is used by the external algorithm depends on the algorithm invoked. The external algorithm interface also defines steps for the algorithm invocation to be saved and later restored by the framework. The interface is able to receive analysis results from the integrated algorithm in the form of graphics, derived parameters, tabular data, gating data (such as in the Gating ML format), classification results files (CLR), XML data, or comma separated values (CSV) files. Said differently, the interface is configured to manage artifacts generated by integrated algorithms.

The interfaces define a contract by which the external algorithms and server functions must adhere to plug the external algorithm into the analysis software. The external algorithm interface and the pre/post processing interface 210 each define a contract for interfacing with pre/post processing on an external server or interfacing with an external algorithm.

Deep Learning Particle Classification

Having outlined the features of a plug-in and related framework for integrating different functionality into the researcher workspace, additional details of the deep learning features will be discussed. The deep learning features may be implemented as a plug-in, or module, to the analytical workbench (e.g., software-based tool or platform) using a framework such as that described above.

The plug-in may facilitate two modes of operation. In one mode, the plug-in may receive event data and generate a new model for classifying one or more particles of interest, such as cells, represented by the measurements included in the event data. Event data may include information obtained from external sources, such as acquisition instrument 140. Event data may also include information stored in one or more datasets. For example, event data may represent measurements generated by an acquisition instrument 140. In a second mode, the plug-in may receive event data and a selection of an existing model for use in generating classifications.

Figure 3:
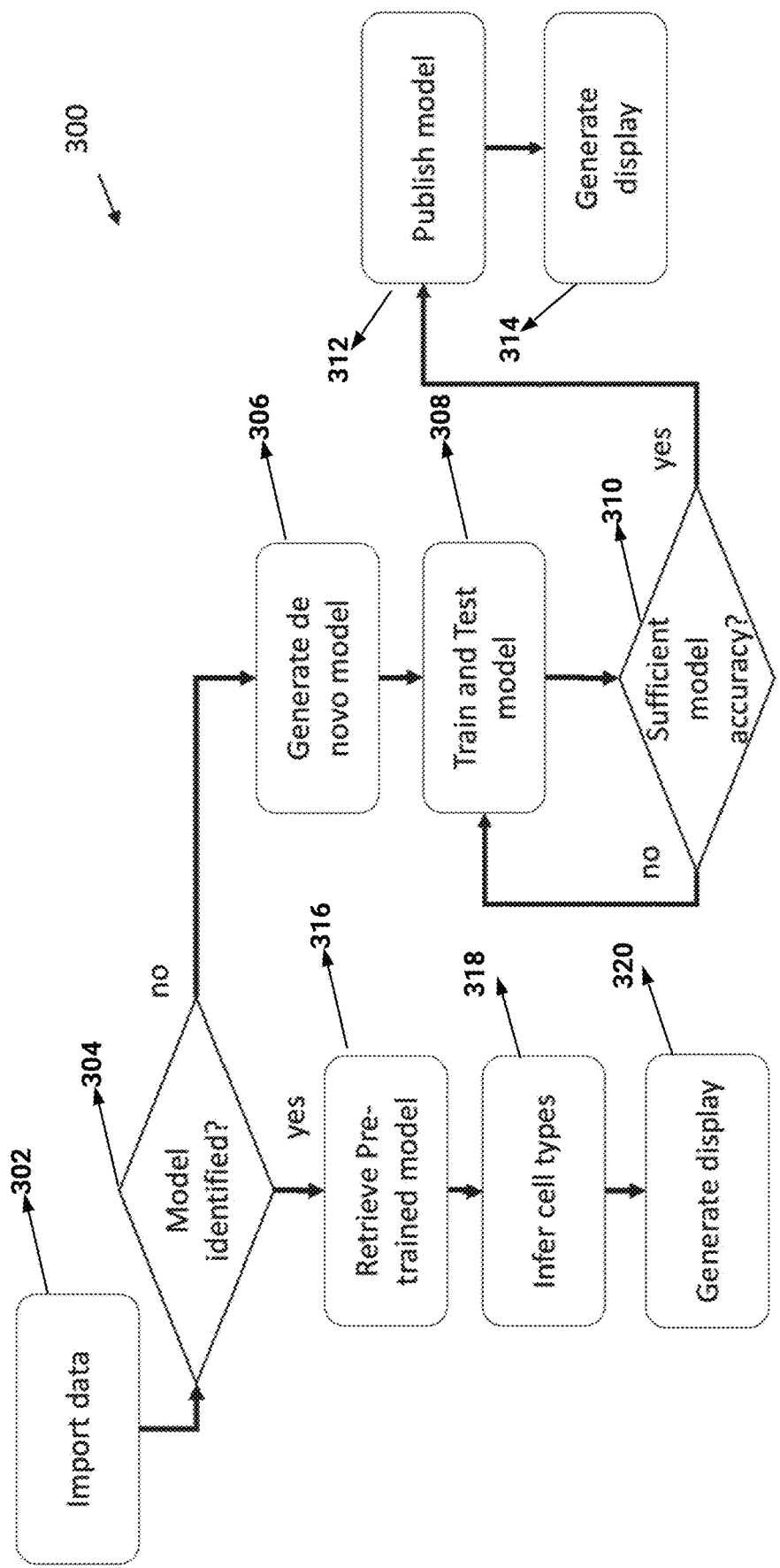
FIG. 3 illustrates a flow diagram of a process for generating a classification display of some embodiments described herein.

FIG. 3 illustrates a flow diagram of a process 300 for generating a classification display. The process 300 may be implemented in whole or in part by one or more of the devices or systems described in this application (e.g., system 100). The process 300 begins at block 302 with the importing of data. The importing of data may be based on information provided via the plug-in to transmit event data to the system. In some implementations, the event data may be received from an acquisition instrument prior to executing the plug-in.

At block 304, the process 300 may then determine whether a model was identified for the imported data. The determination may include receiving a value from the plug-in identifying a model to use. As described above, this determination may be based on the cell populations which are to be sorted. As an example, a particular machine learning model may be advantageous to sort cell populations based on certain phenotypes. If the determination is negative, the process 300 may proceed to generate a de novo model at block 306 (e.g., based on the imported data). Generating a de novo model is described below, with respect to FIG. 4.

Figure 4:
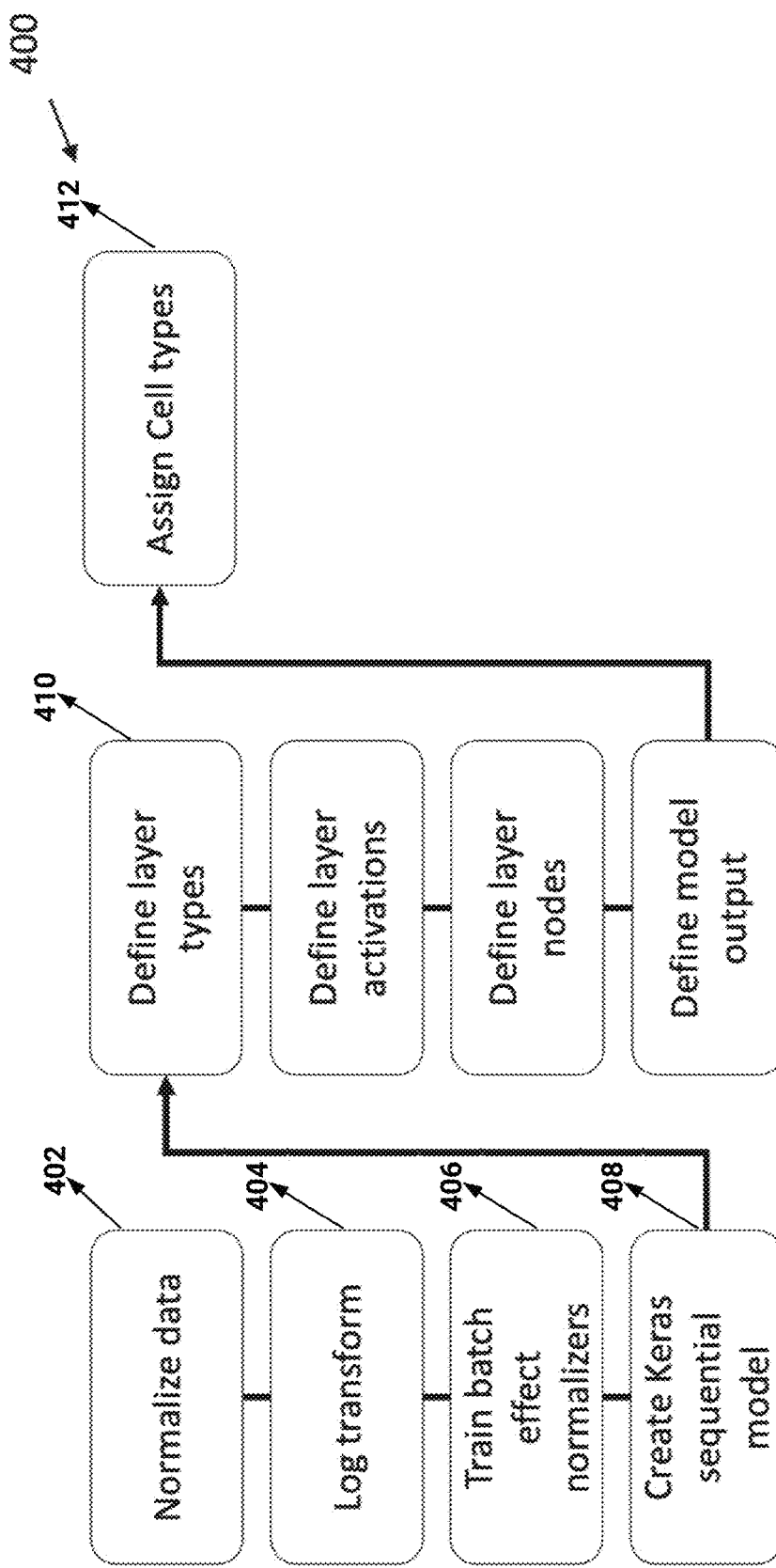
FIG. 4 illustrates a flow diagram of a process for generating a de novo model of some embodiments described herein.

FIG. 4 illustrates a flow diagram of a process 400 for generating a de novo model. The process 400 show in FIG. 4 may be implemented in whole or in part by one or more device described. The coordinating device may begin at block 402 by normalizing the data. In some implementations, the process 400 may include pooling data from multiple experiments to serve as a training data set. To ensure data from different events are properly represented when combined with other experiments, the pooled data may be normalized. For example, normalization may divide the gene or protein counts in each experiment by total gene or protein counts in total pooled data.

Once normalized, at block 404 the process 400 may transform the normalized, pooled data. The transformation may include a log transformation such as a Log10+1 transform of the unique molecular identifier (UMI) counts.

At block 406, Data may be bulk normalized prior to transformation, then normalized again to remove inter-experimental batch effects. This enables deep learning algorithms to treat the pooled data in a similar fashion for training the method without conflating outcomes on the basis of differences in sensitive upstream steps such as sample preparation.

In some instances, the received data may include classification information for events of interest. In such instances, the data may be partitioned whereby one portion is used for training a model and a second portion is used for testing the model. One example is splitting the data set into a 70% training portion and a 30% testing portion. In an example experiment, the data set included 12 Rhapsody experiments, 92 k PBMCs which included an immune gene panel (397 genes)+AbSeq (22 protein markers). The data set also included 10 exemplary immune cell populations (e.g., B, dendritic cells, classical monocytes, non-classical monocytes, gamma-delta T cells, CD4T memory, CD4T naïve, CD8T memory, CD8T naïve, NK). Within the data set, cell types were annotated manually to generate 'true' label to train and test the neural network.

Once the data is ready for training and testing, at block 408 the process 400 may generate the neural network. One way to generate the neural network is using Keras with a TensorFlow backend in Python. At block 410, the model hyperparameters may be generated using a randomized search on the number of neurons, activation function, batch size, and number of epochs. The number may be bounded using a configuration for each or specific model parameters. The number of layers may also be defined in the configuration. For example, a four or five layer neural network appears to provide a reasonable tradeoff between computational complexity, resource utilization, and neural network result accuracy. At block 412, the model may then be used to classify events (e.g., assign cell types).

Table 1 provides a portion of an example neural network model for cell classification generated during experimentation. For example, this example neural network may have been generated using a Keras fronted.

TABLE 1

| Layer (type) | Output Shape | Param # |
|---|---|---|
| dense_7 (Dense) | (None, 128) | 53760 |
| dense_8 (Dense) | (None, 64) | 8256 |
| dense_9 (Dense) | (None, 64) | 4160 |
| dense_10 (Dense) | (None, 32) | 2080 |
| dense_11 (Dense) | (None, 32) | 1056 |
| dense_12 (Dense) | (None, 10) | 330 |

Total params: 69,642
Trainable params: 69,642

Table 2 provides the experimental training and testing results for the model.

TABLE 2

| | Train | Test | |
|---|---|---|---|
| Model | Accuracy | Accuracy | F1-Score |
| mRNA NN | 0.9566 | 0.8728 | 0.8554 |
| AbSeq NN | 0.9383 | 0.9336 | 0.9037 |
| mRNA + AbSeq NN | 0.9648 | 0.9513 | 0.9341 |

Table 3 provides a comparison of the trained neural network model with a random forest classification.

TABLE 3

| mRNA Only | Test | |
|---|---|---|
| Model | Accuracy | F1-Score |
| Neural Net | 0.8728 | 0.8554 |
| Random Forest | 0.8706 | 0.8469 |

Returning to FIG. 3, once the de novo model is generated at block 306, the model may be trained and tested at block 308. The training and testing may include receiving a training data set including expected classifications for events. The events within the training data may then be assessed with the model. The results of the model may be compared with the expected classifications. The difference between the results and expected classifications may be used to generate a metric indicating the accuracy of the model. At block 310, if the accuracy of the model meets a predetermined threshold, then at block 312 the model may be published for use by the plug-in and used to generate a display for the imported data. If the accuracy of the model does not meet the predetermined threshold, then at block 314 process 300 may repeat the training and testing to update the model as described.

At block 316, if the imported data includes identification of a pre-trained model, the pretrained model may be retrieved based on the identification. The pretrained model may be a model that was published after meeting the accuracy threshold. The pretrained model may be stored in a data store accessible by the device coordinating the method. By way of example, a retrained model may include a model associated with a particular set of reagents. For example, a pre-trained model may be developed for T cell classification using a kit comprising a particular panel of antibodies for detecting T cells (such as a CD4 antibody labeled with a first fluorophore and a CD8 antibody labeled with a second fluorophore). The pre-trained model may then be used with that kit to classify T cells.

Once obtained, at block 318 the cell types (e.g., classifications) may be inferred for the imported data and a display generated at block 320. Generating the display may include generating or presenting, via a user interface, model performance, classification of events, and regression results for the data set. In some implementations, the results may flow through the plug-in for presentation via an analytical workbench such as FlowJo. An example presentation is described above, with respect to FIG. 1B.

In this way, the machine learning model may assign classifications to particles such as cells. In some embodiments, the classifications may then subsequently be used. For example, a system may use the classifications to instruct a flow cytometer to sort cell populations according to the classifications. As another example, a system may use the classifications to increase, or decrease, sensitivity of a detector such as an optical detector of a flow cytometer to avoid background. As an example, the system may adjust sensitivity of a detector based on the classifications. Thus, if a detector (e.g., acquisition unit or portion thereof) provides events for analysis, the sensitivity for certain phenotypes (e.g., reagents, surface markers, and so on) may be adjusted to increase an accuracy associated with classifying the provided events.

With respect to the above description of FIGS. 1A-1B and 3-4, neural networks and machine learning models were described. It should be appreciated that machine learning models may include support vector machines, dense (e.g., fully-connected) neural networks, convolutional neural networks, recurrent neural networks, and so on.

In some embodiments, a convolutional neural network may be used to analyze flow cytometry data and or datasets as described herein. It may be appreciated that experienced persons may view graphical representations of such data, for example event data plotted against phenotype information. Example phenotype information may include surface markers and/or gene expression levels and/or protein expression levels. These persons may then perform a gating process. In some embodiments, a convolutional neural network may apply volumes of filters via different layers to learn image features which may enable such automatic gating. For example, the convolutional neural network may be trained based on image data of such gating. In this example, label information associated with cells, cell populations, phenotype information, and so on, may be provided. Thus, certain machine learning models may leverage convolutional neural networks to analyze (e.g., sort) cell populations as described herein.

Figure 5:
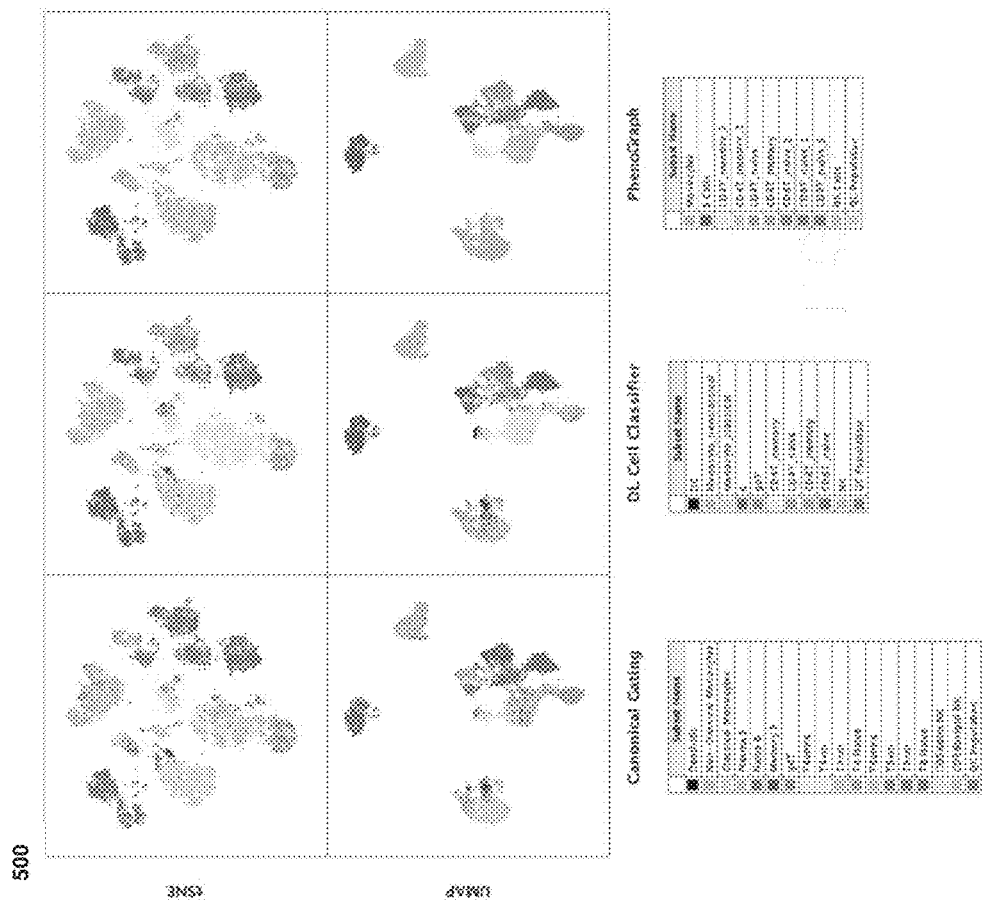
FIG. 5 illustrates visualizations of event data that may be generated by different methods of some embodiments described herein.

FIG. 5 illustrates visualizations of event data 500 that may be generated by different methods. The visualizations shown in FIG. 5 are UMAP and tSNE plots for three different classifiers: (1) human expert canonical gating; (2) the deep learning features described; and (3) existing machine learning using PhenoGraph. As shown in FIG. 5, the deep learning plot provides fewer, but more meaningful, classifications than the canonical gating. FIG. 5 also shows that certain populations overlooked by PhenoGraph are represented (e.g., subset DC, distinguishing between classical and non-classical monocytes).

Figure 6:
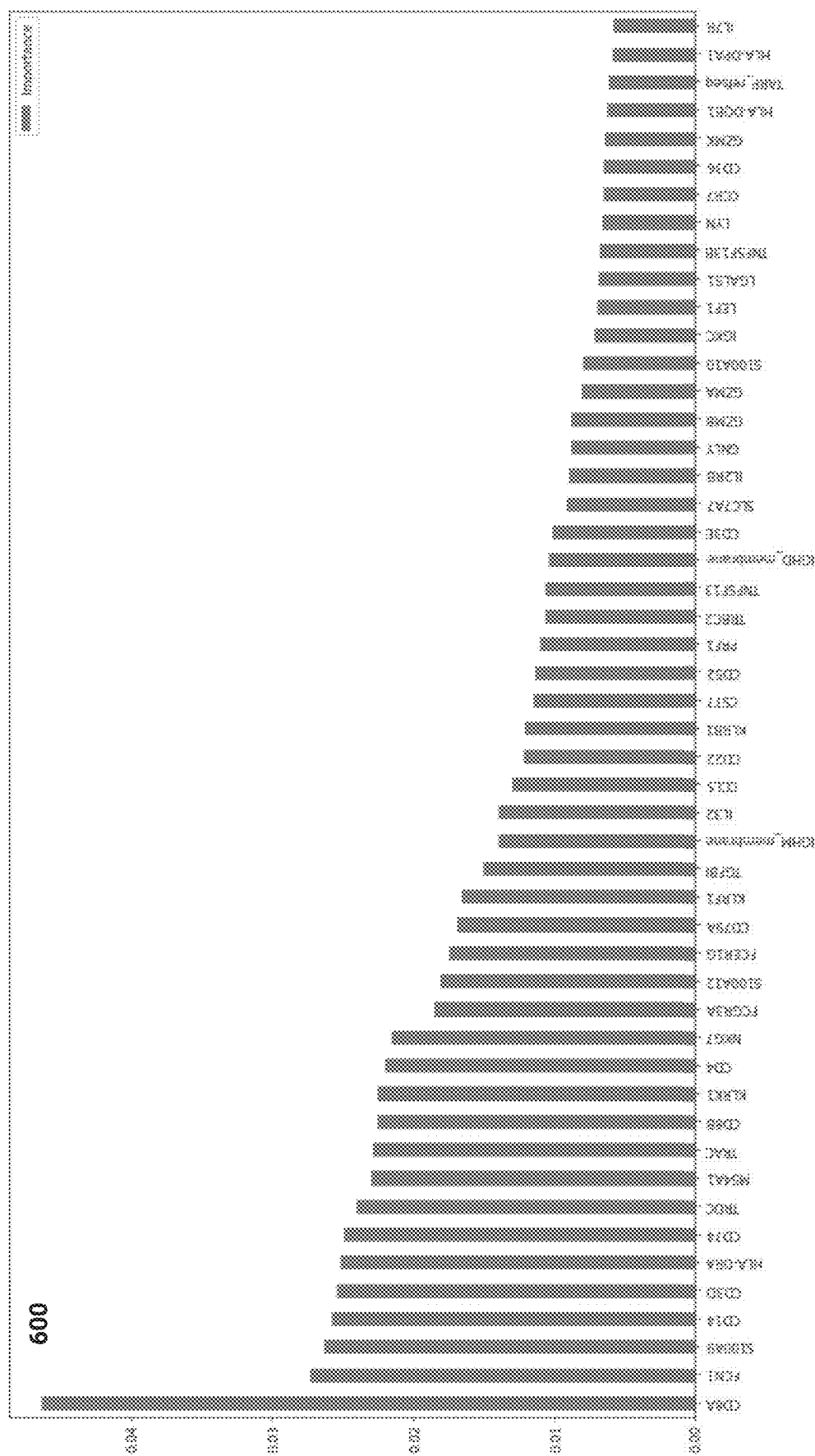
FIG. 6 illustrates a plot of the relative importance of different features which may be used by a model for classifying particles of some embodiments described herein.

FIG. 6 illustrates a plot 600 of the relative importance of different features which may be used by a model for classifying particles of some embodiments described herein. These features can be used in later iterations of a cytometric or other experimental study. For example, the features may be selected for designing targeted panels aimed at identifying specific biological classes. These features also give important feedback to clarify and disambiguate the process by which the deep learning model is working and can be used to generate or train or retrain models. In other words, relatively important features for classification provide useful information in and of themselves; giving rise to potentially novel and verifiable features describing biological states within the deep learning training process.

To illustrate the usefulness of feature importance metrics, in one experiment, the top 100 mRNA and top 8 AbSeq lineage markers were selected based on detected feature importance. These features were then used to build a NN model based on this subset of input variables. The experiment produced a model with high classification accuracy of 95% using only 100 mRNA and 8 AbSeq lineage markers. These results are comparable to a NN model built with 399 mRNA targets and 22 AbSeq lineage markers. Table 4 summarizes the differences between the two models.

TABLE 4

| Model | Train Accuracy | Test Accuracy | F1-Score |
|---|---|---|---|
| mRNA + AbSeq NN (399 genes + 22 proteins) | 0.9648 | 0.9513 | 0.9341 |
| Feature selected mRNA + AbSeq NN (100 genes + 8 proteins) | 0.9651 | 0.9501 | 0.9337 |

Example Embodiments

One example implementation of the features described may include a software plugin for FlowJo's SeqGeq software to predict cell type based on a pre-trained model in Keras with a Tensor Flow backend. The tool may be provided as instructions written in Python, but may be capable of implementation in other languages such as JavaScript. The plug-in may receive identification of a population from SeqGeq, a single-cell bioinformatic data analysis platform, and a model choice as input. The model may be selected from a set of trained models presented via a user interface of the plug-in. The system may include a model publishing feature to receive models for inclusion in the platform. The tool outputs unbiased clusters, based on the model's prediction per cell, annotated with their corresponding cell types, a summary metric of median cell type scores (in a heat-mapped confusion matrix), and gene sets associated with the cell type predicted.

The plug-in may obviate or reduce the need for researchers to tediously annotate populations from dimensionally reduced space (such as tSNE or UMAP) by hand. This can reduce biases associated with cell type characterization. The tool may include feature to identify genes important for researchers such as for use in designing targeted panels. The tool may include advanced machine learning and even deep learning outputs for mapping cell types at a detail and nuance beyond what is practical by manual classification. For example, researchers currently need to rely on certain known, key features of populations (e.g., a canonical marker, or gene set) to distinguish one cell type from the other. This a priori knowledge is used to investigate each of those features independently and can lead to biased choices for cell typing. In contrast, the plug-in may identify the populations based on pre-trained models which can objectively and discriminately identify events related to the populations.

As used herein, "system," "instrument," "apparatus," and "device" have their customary and ordinary meaning as understood by one of ordinary skill in the art in view of this disclosure. They generally encompass both the hardware (e.g., mechanical and electronic) and, in some implementations, associated software (e.g., specialized computer programs for graphics control) components.

As used herein, an "event" has its customary and ordinary meaning as understood by one of ordinary skill in the art in view of this disclosure. It generally refers to the data measured from a single particle, such as cells or synthetic particles. Typically, the data measured from a single particle (such as a cell) include a number of parameters, including one or more light scattering parameters, and at least one fluorescence intensity parameters. Thus, each event is represented as a vector of parameter measurements, wherein each measured parameter corresponds to one dimension of the data space. In some biological applications, event data may correspond to quantitative biological data indicating expression of a particular protein or gene.

As used herein, a "population", or "subpopulation" of particles, such as cells or other particles, have their customary and ordinary meaning as understood by one of ordinary skill in the art in view of this disclosure. They generally refer to a group of particles that possess optical properties with respect to one or more measured parameters such that measured parameter data form a cluster in the data space. Thus, populations are recognized as clusters in the data. Conversely, each data cluster generally is interpreted as corresponding to a population of a particular type of cell or particle, although clusters that correspond to noise or background typically also are observed. A cluster may be defined in a subset of the dimensions, e.g., with respect to a subset of the measured parameters, which corresponds to populations that differ in only a subset of the measured parameters.

As used herein, a "gate" has its customary and ordinary meaning as understood by one of ordinary skill in the art in view of this disclosure. It generally refers to a boundary identifying a subset of data (e.g., particle measurements) of interest. In cytometry, a gate may bound a group of events of particular interest. The group of events may be referred to a population. Further, as used herein, "gating" may generally refer to the process of defining a gate for a given set of data such as via a user interface or plate and well selections.

As used herein, the terms "determine" or "determining" have their customary and ordinary meaning as understood by one of ordinary skill in the art in view of this disclosure.

They encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" have their customary and ordinary meaning as understood by one of ordinary skill in the art in view of this disclosure. They encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, the term "selectively" or "selective" have their customary and ordinary meaning as understood by one of ordinary skill in the art in view of this disclosure. They may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the term "message" has its customary and ordinary meaning as understood by one of ordinary skill in the art in view of this disclosure. It encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein a "user interface" (also referred to as an interactive user interface, a graphical user interface, an interface, or a UI) has its customary and ordinary meaning as understood by one of ordinary skill in the art in view of this disclosure. It may refer to a network based interface including data fields and/or other controls for receiving input signals or providing electronic information and/or for providing information to the user in response to any received input signals. A UI may be implemented in whole or in part using technologies such as hyper-text mark-up language (HTML), ADOBE® FLASH®, JAVA®, MICROSOFT® .NET®, web services, and rich site summary (RSS). In some implementations, a UI may be included in a stand-alone client (for example, thick client, fat client) configured to communicate (e.g., send or receive data) in accordance with one or more of the aspects described.

As used herein, a phrase referring to "at least one of" a list of items has its customary and ordinary meaning as understood by one of ordinary skill in the art in view of this disclosure. It refers to any combination of those items, including single members. As an example, "at least one of: a, b, or c" is intended to cover: a, b, c, a-b, a-c, b-c, and a-b-c.

Those of skill in the art would understand that information, messages, and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Additional Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 7:
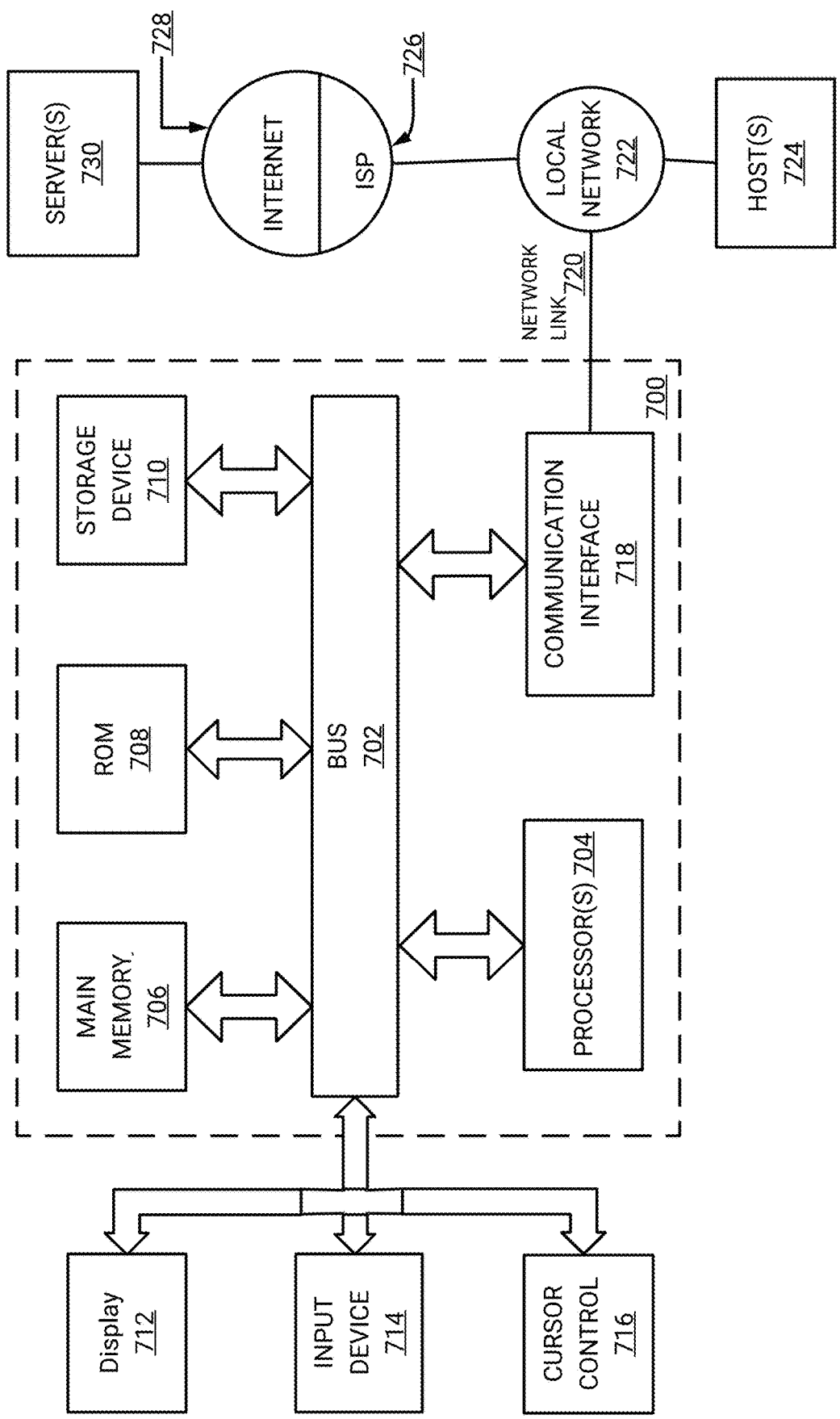
FIG. 7 is a block diagram that illustrates a computer system upon which various embodiments may be implemented.

For example, FIG. 7 is a block diagram that illustrates a computer system 700 upon which various embodiments may be implemented. Computer system 700 includes a bus 702 or other communication mechanism for communicating information, and a hardware processor, or multiple processors, 704 coupled with bus 702 for processing information. Hardware processor(s) 704 may be, for example, one or more general purpose microprocessors.

Computer system 700 also includes a main memory 706, such as a random access memory (RAM), cache and/or other dynamic storage devices, coupled to bus 702 for storing information and instructions to be executed by processor 704. Main memory 706 also may be used for storing temporary variables or other intermediate information during execution of instructions to be executed by processor 704. Such instructions, when stored in storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk, optical disk, or USB thumb drive (Flash drive), etc., is provided and coupled to bus 702 for storing information and instructions.

Computer system 700 may be coupled via bus 702 to a display 712, such as a cathode ray tube (CRT) or LCD display (or touch screen), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 700 may include a user interface module to implement a GUI that may be stored in a mass storage device as computer executable program instructions that are executed by the computing device(s). Computer system 700 may further, as described below, implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor(s) 704 executing one or more sequences of one or more computer readable program instructions contained in main memory 706. Such instructions may be read into main memory 706 from another storage medium, such as storage device 710. Execution of the sequences of instructions contained in main memory 706 causes processor(s) 704 to perform the process steps described herein. In alternative embodiments, hard-wired circuitry may be used in place of or in combination with software instructions.

Various forms of computer readable storage media may be involved in carrying one or more sequences of one or more computer readable program instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN (or WAN component to communicated with a WAN). Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computing system in data communication with a source of events comprising flow cytometry data, the computing system being implemented for sorting cell populations according to phenotype, and the computing system comprising:
    one or more computer processors; and
    non-transitory computer-readable media storing instructions that, when executed by the one or more computer processors, cause the computing system to perform operations comprising:
        executing a software-platform associated with analyzing received events, the received events being obtained via an acquisition device in communication with the computing system, and the software-platform sorting cell populations indicated in the events;
        causing presentation, via the software-platform, of an interactive user interface, wherein the interactive user interface:
        receives user input indicating selection of a deep-learning module, the deep-learning module being obtained via a network to supplement the software-platform,
            wherein, based on the received events, the deep-learning module determines whether to select a machine learning model of a plurality of machine learning models accessible via the software-platform, wherein the selection is based on same similarities between phenotypes indicated in the events as phenotypes used for training the machine learning models, and wherein the phenotypes include, at least, surface markers,
            wherein upon a positive determination of selection of a machine learning model, the interactive user interface presents information identifying the selected machine learning model,
            and wherein upon a negative determination of selection of a machine learning model, the deep-learning module is configured to aggregate the events and train a new machine learning model, wherein the aggregated events include the received events and events associated with one or more users of the software platform, wherein the aggregated events are bulk normalized via performance of a transformation of unique molecular identifiers (UMI) counts and subsequently normalized to remove inter-experimental batch effects, wherein based on an accuracy associated with the new machine learning model exceeding a threshold, the deep-learning module is configured to select the new machine learning model and to upload the new machine learning model to an online repository for access by users of the software platform;

applying the selected machine learning model via generating a forward pass of information generated based on the events, the information being normalized based on the events; and presenting, via the interactive user interface, a graphical representation of cell populations indicated in the events, the graphical representation sorting the cell populations according to phenotypes, wherein the interactive user interface is updated to include the graphical representation in an analysis portion.

2. The computing system of claim 1, wherein the phenotypes further include surface receptors, antigens, gene expression levels, and/or protein expression levels.

3. The computing system of claim 1, wherein the deep-learning module accesses the online repository which includes the machine learning models, and wherein the machine learning models were created by the users of the software-platform.

4. The computing system of claim 1, wherein the graphical representation comprises a graphical depiction of gating of the events.

5. The computing system of claim 1, wherein a machine learning model comprises a fully-connected neural network or a convolutional neural network.

6. A method implemented by a computing system of one or more processors, the method comprising:

executing a software-platform associated with analyzing received events comprising single cell phenotype data, the received events being obtained via an acquisition device or based one or more datasets stored by a database, and the software-platform sorting cell populations indicated in the events;

causing presentation, via the software-platform, of an interactive user interface, wherein the interactive user interface:

receives user input indicating selection of a deep-learning module, the deep-learning module being obtained via a network to supplement the software-platform, wherein, based on the received events, the deep-learning module determines whether to select a machine learning model of a plurality of machine learning models accessible via the software-platform, wherein the selection is based on same similarities between phenotypes indicated in the events as phenotypes used for training the machine learning models, and wherein the phenotypes include, at least, surface markers, wherein upon a positive determination of selection of a machine learning model, the interactive user interface presents information identifying the selected machine learning model, and wherein upon a negative determination of selection of a machine learning model, the deep-learning module is configured to aggregate the events and train a new machine learning model, wherein the aggregated events include the received events and events associated with one or more users of the software platform, wherein the aggregated events are bulk normalized via performance of a transformation of unique molecular identifiers (UMI) counts and subsequently normalized to remove inter-experimental batch effects, wherein based on an accuracy associated with the new machine learning model exceeding a threshold, the deep-learning module is configured to select the new machine learning model and upload the new machine learning model to an online repository for access by users of the software platform;

applying the selected machine learning model via generating a forward pass of information generated based on the events, the information being normalized based on the events; and presenting, via the interactive user interface, a graphical representation of cell populations indicated in the events, the graphical representation sorting the cell populations according to phenotypes, wherein the interactive user interface is updated to include the graphical representation in an analysis portion.

7. The method of claim 6, wherein the phenotypes further include surface receptors, antigens, gene expression levels, and/or protein expression levels.

8. The method of claim 6, wherein the deep-learning module accesses the online repository which includes the machine learning models, and wherein the machine learning models were created by the users of the software-platform.

9. The method of claim 6, wherein the graphical representation comprises a graphical depiction of gating of the events.

10. The method of claim 6, wherein a machine learning model comprises a fully-connected neural network or a convolutional neural network.

11. Non-transitory computer storage media storing instructions that when executed by a system of one or more processors, cause the one or more processors to perform operations comprising:

executing a software-platform associated with analyzing events obtained via an acquisition device or based one or more datasets stored by a database, the software-platform sorting cell populations indicated in the events;

causing presentation, via the software-platform, of an interactive user interface, wherein the interactive user interface:

receives user input indicating selection of a deep-learning module, the deep-learning module being obtained via a network to supplement the software-platform, wherein, based on the received events, the deep-learning module determines whether to select a machine learning model of a plurality of machine learning models accessible via the software-platform, wherein the selection is based on same similarities between phenotypes indicated in the events as phenotypes used for training the machine learning models, and wherein the phenotypes include, at least, surface markers, wherein upon a positive determination of selection of a machine learning model, the interactive user interface presents information identifying the selected machine learning model, and wherein upon a negative determination of selection of a machine learning model, the deep-learning module is configured to aggregate the events and train a new machine learning model, wherein the aggregated events include the received events and events associated with one or more users of the software platform, wherein the aggregated events are bulk normalized via performance of a transformation of unique molecular identifiers (UMI) counts and subsequently normalized to remove inter-experimental batch effects, wherein based on an accuracy associated with the new machine learning model exceeding a threshold, the deep-learning module is configured to select the new machine learning model and upload the new machine learning model to an online repository for access by users of the software platform;

applying the selected machine learning model via generating a forward pass of information generated based on the events, the information being normalized based on the events; and presenting, via the interactive user interface, information identifying assignments of respective classifications to the events, individual classifications reflecting individual cell types, and the assignments being based on output of the selected machine learning model, wherein the interactive user interface is updated to include the information in an analysis portion.

12. The computer storage media of claim 11, wherein phenotypes further include surface receptors, antigens, gene expression levels, and/or protein expression levels.

13. The computer storage media of claim 11, wherein the deep-learning module accesses the online repository which includes the machine learning models, and wherein the machine learning models were created by the users of the software-platform.

14. The computer storage media of claim 11, wherein the operations further comprise:
instructing a flow cytometer to sort cell populations according to the assigned classifications.

15. The computer storage media of claim 11, wherein the operations further comprise:
adjusting sensitivity of the acquisition device based on the classifications.

16. The computing system of claim 1, wherein the operations further comprise:
instructing a flow cytometer to sort cell populations according to the assigned classifications.

17. The computing system of claim 1, wherein the operations further comprise:
adjusting sensitivity of the acquisition device based on the classifications.

18. The method of claim 6, further comprising:
instructing a flow cytometer to sort cell populations according to the assigned classifications.

19. The method of claim 8, further comprising:
adjusting sensitivity of the acquisition device based on the classifications.

* * * * *